United States Patent [19]

Ralph

[11] E Re. 28,483

[45] Reissued July 15, 1975

[54] SANITARY GARMENT FOR INCONTINENT PERSONS

[76] Inventor: Harold J. Ralph, 2002 E. Santa Clara St., Apt. M-1, Santa Ana, Calif. 92701

[22] Filed: Aug. 14, 1970

[21] Appl. No.: 63,958

Related U.S. Patent Documents

Reissue of:

[64] Patent No.: 3,441,025
Issued: Apr. 29, 1969
Appl. No.: 452,056
Filed: Apr. 30, 1965

[52] U.S. Cl. ..... 128/289
[51] Int. Cl. ..... A61f 5/44
[58] Field of Search ..... 128/284, 286, 287–291

[56] References Cited

UNITED STATES PATENTS

| | | | |
|---|---|---|---|
| 474,378 | 5/1892 | Ferguson | 128/286 |
| 1,159,362 | 11/1915 | Cornell | 128/289 |
| 1,276,238 | 8/1918 | Lowder | 128/291 |
| 1,664,626 | 4/1928 | Ito | 128/286 |
| 2,444,973 | 7/1948 | Best | 128/287 |
| 2,545,674 | 3/1951 | Ralph | 128/287 |
| 2,575,164 | 11/1951 | Donovan | 128/287 |
| 2,575,165 | 11/1951 | Donovan | 128/287 |
| 2,616,427 | 11/1952 | Petit | 128/289 |
| 2,662,526 | 12/1953 | Sanford | 128/287 |
| 2,685,879 | 10/1954 | Emmet | 128/287 |
| 2,914,069 | 11/1959 | Osborn | 128/287 |
| 2,977,957 | 4/1961 | Clyne | 128/291 |
| 3,042,043 | 7/1962 | Wuhrlin | 128/284 |
| 3,094,990 | 6/1963 | Neilson | 128/289 |
| 3,103,930 | 9/1963 | Collett et al. | 128/286 |

*Primary Examiner*—Richard A. Gaudet

[57] ABSTRACT

A sanitary garment for incontinent persons including a moisture impervious flexible holder cover having side-edge and end flaps providing a reservoir for receiving absorbent pads and wherein the flaps are foldable thereover so that the pads are supported within a moisture impervious reservoir. A belt serves to support the cover and pads as a protective garment between the crotch and from the waist of the wearer.

8 Claims, 9 Drawing Figures

2 Sheets-Sheet 1

INVENTOR
HAROLD J. RALPH
BY
ATTORNEY

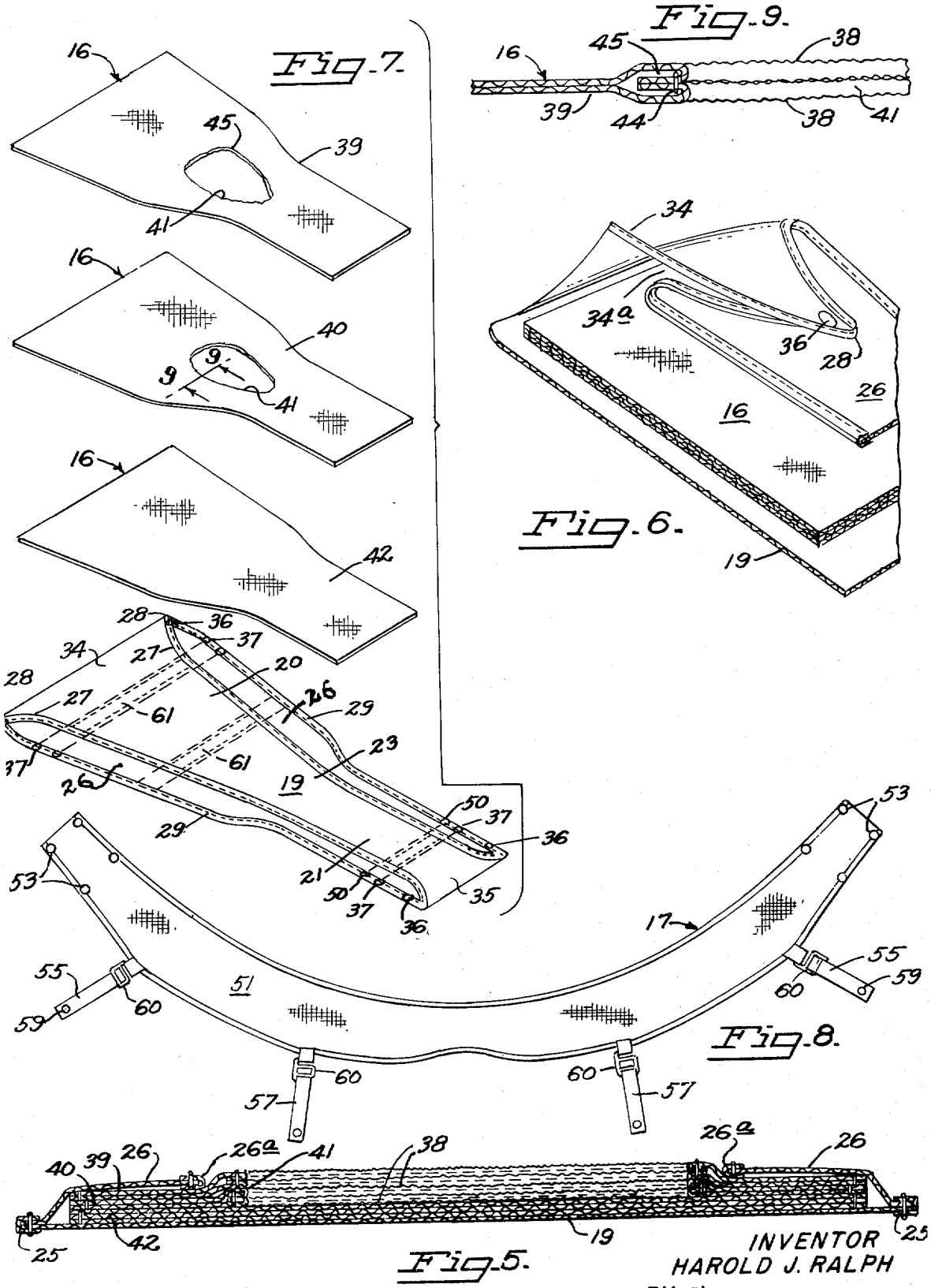
INVENTOR
HAROLD J. RALPH
BY Jas. S. Graham
ATTORNEY

SANITARY GARMENT FOR INCONTINENT PERSONS

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to sanitary garments for incontinent persons, within the meaning of uncontrollable discharge. More particularly the invention relates to such a flexible launderable garment impervious to leakage, fitted to the anatomy in the area of the hips and crotch, and having readily replaceable absorbent pads which are convenient for replacement and laundering.

It is well known that there are persons who may have a weakness or lack of efficient control of personal discharge from either the rectum or urinal outlet. Such lack of control is generally referred to as incontinence, and the persons so troubled may be referred to as being incontinent. The difficulty may affect either ambulatory or bedridden persons, and it is anticipated that in its various degrees such a condition may be mildly inconvenient or exceedingly troublesome in the care and treatment of either ambulatory or bedridden patients.

2. Description of the Prior Art

Absorbent pads incorporated into bloomer-like hip-enclosing garments have been tried, but have been found bulky, lacking in ventilation of the enclosed and covered skin, producing chafing and discomfort, inclined to drip the pad into the enclosing bloomer garment, difficult to launder and change to a replacement garment, and usually of a bulk visible from the exterior of ordinary clothing of ambulatory patients.

SUMMARY OF THE INVENTION

Among the objects of the invention is to provide a suitably supported moisture impervious garment including a holder cover and an absorbent pad for accommodation of discharge of incontinent persons, and snugly fitting the anatomy of the wearer.

Another object is to provide in such a garment a convenient efficient means for detachably supporting on the body of the wearer an impervious holder of an absorbent pad.

A further object is to provide a highly absorptive pad and garment, in which the parts may be readily laundered and handled for washing.

A further object is to provide such a garment for incontinent persons which provides exposure of a maximum area of adjacent cuticle to ventilation of atmospheric air.

Another object is to provide for such a personal use, a pad having high absorptive qualities and readily installed, changeable and comfortable in wearing, as well as providing means by which discharge of excretions may be localized.

BRIEF DESCRIPTION OF THE DRAWINGS

With the foregoing and other objects in view, a preferred form of the invention is described in the following specification and illustrated in the accompanying drawings in which:

FIG. 5 is an enlarged lateral transverse section on line 5—5 of FIG. 3.

FIG. 6 is a fragmentary diagrammatic perspective sectional view of an upper right hand corner of the garment of FIG. 3, with a retroverted end-flap member in unfastened position.

FIG. 7 is a perspective assembly view of constituent pads and holder member.

FIG. 8 is a plan view of a supporting belt member.

FIG. 9 is an enlarged fragmentary view of portion of a pad on line 9—9 of FIG. 7.

DETAILED DESCRIPTION OF THE DRAWINGS

Figure 2:
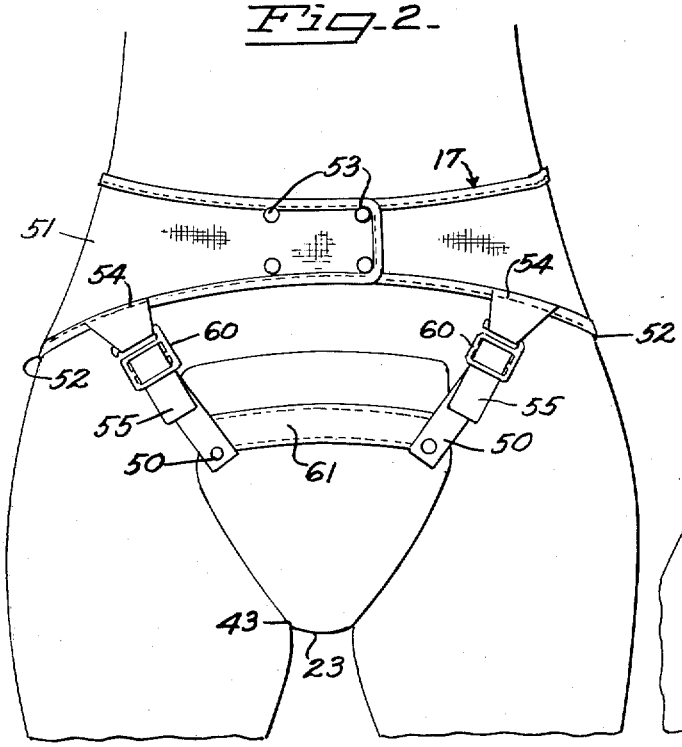
FIG. 2 is a front elevation of FIG. 1.

Referring to the drawings in which like reference characters indicate corresponding parts in the several views, basically the completed garment comprises three parts which are generally indicated as a cover or holder 15, a pad or pads 16, and means for supporting the holder and pads upon the person, such as belt 17.

The holder 15 comprises a sheet of moisture impervious vinyl plastic material flexible in its entirety and of a formulation that is tough and will withstand repeated laundering, and resistant to deterioration from frictional rubbing as well as from either the acids of alkalinity of the human discharges with which the pad normally comes into contact by its use.

This sheet structure of the holder 15 is elongated and comprises a back sheet generally indicated 19, having side flaps 26 connected along its longitudinal edges. The back sheet 19 has one end portion 20 relatively wide transversely which may be termed the rump portion, and an opposite end portion 21 which is relatively narrow transversely, and may be termed the abdomen portion. The wider end portion 20 has its opposite longitudinal side edges 24 converging relatively from the wider free end toward a longitudinal central crotch portion 23, and has its opposite relatively narrower end portion 21 provided with side edges substantially relatively parallel. Adjacent the central crotch portion 23, the back sheet and holder have an accentuated inward taper of the longitudinal side edges at the juncture 22 of said opposite end portions, which may taper into the central crotch portion 23, exemplified as 25° to the longitudinal center line of the holder.

Along the entire length of each of the opposite longitudinal side edges 24 of the back sheet 19 there is imperviously connected, as at 25, one edge of flexible elongated relatively narrow side-edge flaps 26 which freely overlie the relatively opposite side edge portions of the back sheet for a substantial area and have their opposite or inner edges 26*a* free, thus leaving the longitudinal central area of the back sheet freely exposed. Preferably these side flaps 26 are of greater width at the wider end portion 20 of the holder than at the narrower portion 21 and at the central crotch portion 23. At the opposite ends of the side flaps 26 the free edges thereof have an outward arcuate curve 27 to the corner juncture 28 of the longitudinal side edges and the transverse end edges of the back sheet. These side flaps 26 are of substantially the same flexible impervious tough vinyl plastic material as the back sheet 19. The impervious connection of the side flaps to the back sheet may be by any well known plastic-welding process, but is preferably by an edging of cotton tape 29 and suitably stitched, which may also be a common finish to other exposed edges of the vinyl sheet, though manifestly plastic welding may also be employed for any or all such connections or edgings. The cotton strip edging 29 is preferred because it launders extremely efficiently and provides a softer edge against the human skin, and will normally generally outlast a plastic edge, since it becomes softer and smoother with use and age, whereas a welded plastic edge may harden and have rough spots after repeated washing and drying. The opposite end edges 31 of the plastic back sheet which are free and not connected to another part of the holder may be optionally finished with plastic welds or any overlocked thread stitch 32, preferably the latter.

Since the holder is to receive therein pads 16, (to be further described), it is here noted that the length of the back sheet, in planar form, is of greater length than the pads 16 which are mounted in the holder, such surplus of length providing end-flaps indicated 34, 35, wherein the back sheet may be retroverted upon itself and thus provide impervious sealed pockets **34*a*, 35*a*, at the opposite ends of the back sheet, which pockets receive therein the opposite ends of the relatively shorter pads 16 with the retroverted ends 34, 35 folded thereover. In thus folding over the opposite ends 34, 35 of the back sheet, it is to be noted that the adjacent end portion of the side flaps 26 and the imperviously sealed edge 25 are also folded over, thus completing the impervious seal of pockets 34*a*, 35*a* at each corner of the holder member 15**.

Completing the description of holder 15 there are snap-fastener buttons 36 adjacent each end of each side edge of the holder, and corresponding snap-eyelets 37 at the edge portion of the back sheet so that the end flaps 34, 35 may be suitably held in place to form the end pockets **34*a*, 35*a***.

Removable pads, heretofore generally indicated 16, are provided to cooperate with the holder 15 and its back sheet, the side flaps 26 and end pockets **34*a*, 35*a*, and also with a belt support means 17** to be described.

Figure 4:
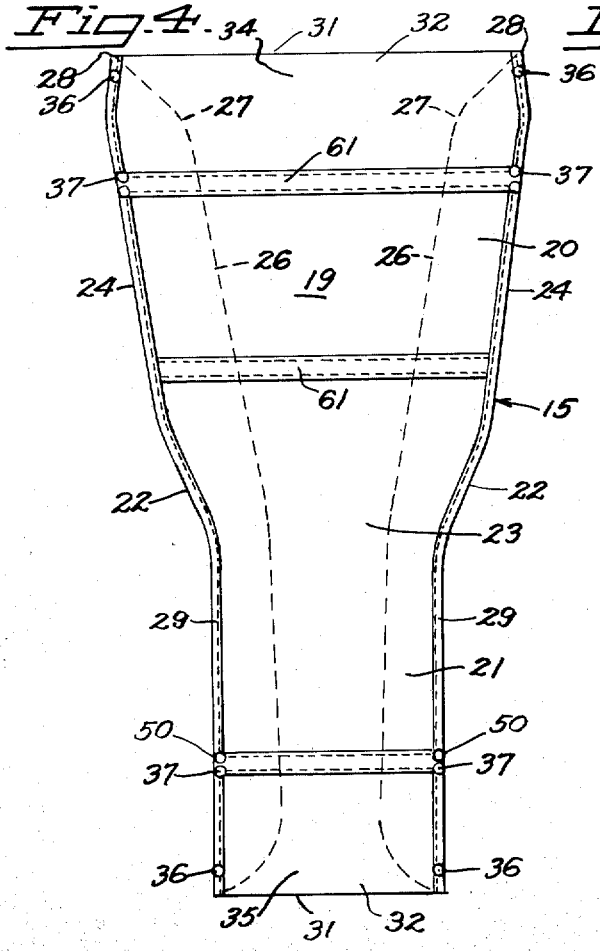
FIG. 4 is a plan view of reverse face of holder member shown in FIG. 3, with ends of back sheet extended its full length.
Figure 3:
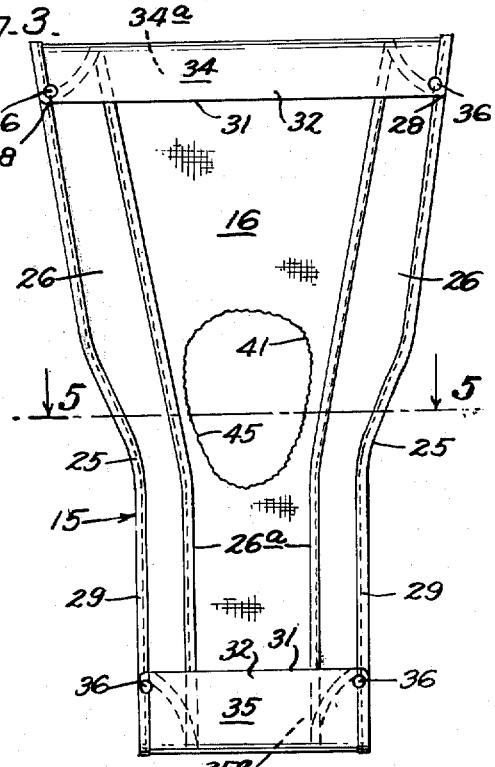
FIG. 3 is a front plan view of a completed garment of the invention.

The pads generally indicated 16 are of soft and absorbent material, and may be of the disposable type or of the readily launderable type, such as cotton. Their peripheral outline conforms to a convenient snugly slidable fit within the holder in overlying relation to the back sheet 19, and underlying the side flaps 26 and the retroverted end members 34, 35. Thus, the pads are shorter than the overall length of the back sheet 19 as shown in FIG. 4. Preferably, in use, more than one pad is employed simultaneously in the holder, the plurality of pads being employed in relatively overlying relation. A plurality of pads are preferred because such a plurality permits adjustment of pad structures for persons who may have differing degrees of aggravated conditions, or who use the entire pad structure for varying uses, and for the further reason that a plurality of overlying pads by irregularity of their opposed surfaces provide interstitial spaces 38 between a plurality of pad layers, into which may seep quantities of liquid fecal or liquid discharge, as will be further mentioned. Facility in laundering and drying of several thin pads as compared with one thick pad also is a further advantage of the use of several superposed washable pads, as well as permitting adjustment of the number of superposed pads to the special need of a particular person.

Suitable types of pads are shown in the collective view of FIG. 7, in which pads 39 and 40 have a central opening 41 in the planar area, and pad 42 has a continuous planar area without such a central opening. The central opening is for the obvious purpose of providing a sump or retaining well in overlying pads to receive and localize discharge of stool, commonly referred to as B. M., in order to prevent its spread over the adjacent surrounding surface of the user of the pad, whereas with some users whose uncontrolled discharge is solely urinal, a single or plurality of superposed layers of pad 42 without the central opening 41 is preferred. It is to be understood that while a pad or pads of any suitable disposable type and material may be entirely practical and suitable in the holder 14, it is preferred that these pads 16 shall each be made of two or more congruent overlying layers of relatively thin soft absorbent material rather than a single layer of relatively thick material, since the double layer of thin material provides an advantage of softness especially at the crimped area of the crotch 23, as well as facilitating laundering and drying. Where the pads have a central planar opening 41, it is to be noted that there is a sewed seam 44 around the area of the opening in between the two superposed layers of the pad. Such an internal seam may be formed by sewing the two layers together around the edges of the opening, whereupon the layers of the pad are turned inside out which may be accomplished by sewing one-half circumferentially of the opening at one time and then turning the layers inside out so that the seam 44 is within the layers of the pad and invisible from the exterior of the pad, thus serving two purposes of preserving the softness of the pad in the area of the crotch and also forming a puckered edge 45 which, when two such pads are juxtaposed in overlying use, provide interstices 38 between the overlying edges of the opening 41 of the superposed pads, for facilitating the spread and absorption of liquid or soft fecal matter.

These pads 16 are of a planar size so that their transverse width fits snugly and slidably in overlying relation to the back sheet and within the longitudinal side edges of the back sheet so that the side flaps 26 and free edges **26*a* may conveniently fold flatly and freely over such pads. The pads are of a length sufficiently shorter than the length of the back sheet 19 so that when the end members 34, 35 including the imperviously-connected end portions of side flaps 26, are retroverted thereover, said retroverted end members may be connected to the back-sheet by the snap fasteners 36, 37, whereby there are provided moisture impervious reservoir corner pockets at the opposite sides of pockets 34*a* 35*a*** of the opposite ends of the holder, with the edge portions of the pad therein.

It may be desirable to provide different sizes of the garment to better accommodate large and small persons. As an illustrative example of relative proportions of a satisfactory size, the back sheet of the holder 15 may have an overall length of 25 inches, the fold-over portions 34, 35 may have a width of 2¼ to 2½ inches (longitudinal of the holder), so that in use the holder and pads would have a length of substantially 20 inches. The maximum width at the wider end portion 20 of the holder may be 12 inches and tapering to a width of 9 inches adjacent the crotch portion 23; the narrower end portion 21 of the holder having a substantially uniform width of 6½ inches, with the accentuated converging taper of side edges between the wider portion 20 and narrower portion 21 being substantially 25° to center line of the holder, as previously stated. The crotch portion 23 is preferably of said narrower dimension of width to facilitate passing thereof between the legs. In the wider part of the holder the overlying side flaps 26 may conveniently have a width of 2½ inches, whereas in the narrow end portion 21 and in crotch portion 23, the side flaps may conveniently have a width substantially 1¾ inches. Manifestly, this dimension for the crotch portion 23 is wider than the normal crotch portion of human anatomy, but the above width is practical for an adult person and provides, firstly, for a condensing or impacting of the width of the absorptive pad at a critical part of the garment, and secondly, it provides an inward pressure on the side flaps 26 at the crotch, which insures that the side flaps will be maintained overlying the pad and thus maintain an impervious reservoir within the holder 15.

Referring now to the belt support 17, it will be observed from FIG. 4 that on the outer face of the back sheet which is the reverse from the flaps 26 and the snap fasteners 36, 37, there are provided at the opposite side edges and adjacently spaced from opposite ends of the holder 15, other snap fasteners 50 which cooperate with the belt support means 17 to be described.

Figure 1:
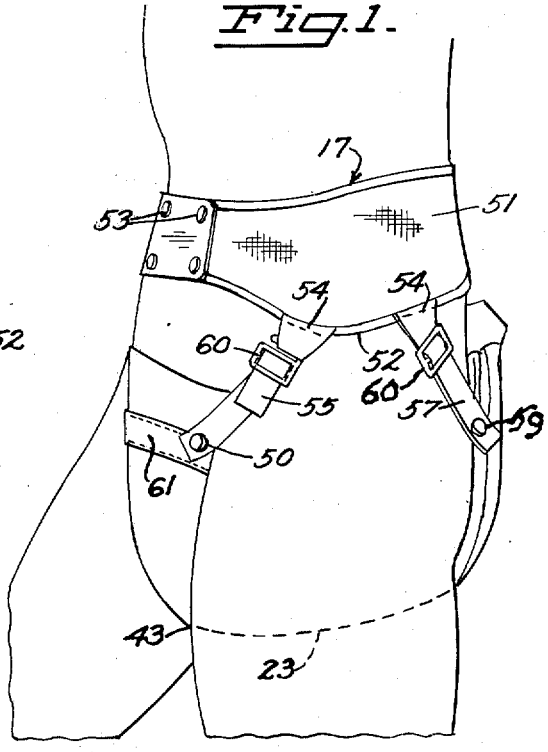
FIG. 1 is a perspective view of the invention shown mounted in operative position.

The belt means heretofore generally indicated 17, is provided for supporting the holder 15 and pad 16 in their appropriate positions as a protective garment, which manifestly contemplates that the broader portion 20 of the pad will be in superficial contact with the derriere, and with the narrow central portion 23 within the crotch, and the narrow end portion 21 extending upwardly to overlie the lower portion of the abdomen adjacent the crotch, as best shown in FIGS. 1 and 2. Such belt support means is best illustrated in the plan view of FIG. 8 as a snugly form-fitting abdominal belt portion 51 contoured to conveniently and snugly encircle the loin or waist portion of the body of the wearer immediately above the hips. The belt has a downward dip portion 52 at lower edged portions, adapted to dip over the opposite hips. At opposite cooperating ends, the belt is provided with any suitable type of releasable fastening means to secure it around the waist, such as snap fasteners 53. The belt may be of any suitable washable material.

At the lower edge of each of the downward dip portions 52 of the belt, over each of the opposite hips, the belt has a relatively spaced front pair and a relatively spaced rear pair of flexible elastic suspenders connected to the belt, such as by sewing 54. The front pair of suspenders are indicated at 55, and are relatively spaced and disposed angularly so that in use they are positioned in the valley of the body of the wearer between the abdomen and thigh. The rear pair of suspenders 57 are likewise relatively spaced and each suspender has one end sewed to the belt at 54 so that in use the rear suspender will overlie the opposite side faces of the rump and extend convergingly downwardly sufficiently so that snap fasteners 59 may releasably engage and cooperate with snap fastener members 50 on the wider or rump portion of the holder. Each of these suspender members, both front and rear, are preferably provided with suitable means for adjustment of its length, such as the buckles indicated 60. Such buckles also provide a means whereby the elastic portion of the suspenders may be detached during laundering of the belt. The tension of the elasticity of these suspenders 55, 57 serves the double purpose of supporting the holder and pad in operative wearing position, and also tensions or draws up the most vulnerable crotch portion of the holder and side flaps 26 tightly against the body in the crotch to prevent leakage during a period of an initial flush discharge in the holder, and until the pad may absorb such flush of liquid.

It is to be observed that the longitudinally extended front and rear suspenders not only releasably support the holder and pads, but also provide open exposure to atmosphere of body portions at hips and thighs, as well as saving the material which, in the usual diapering device, covers the hips and thighs, which it is one of the objects of this invention to eliminate.

If desired, reinforcing strips 61 of cloth tape may extend transversely across the plastic back sheet to serve as a reinforcement and to relieve the strain of wear or laundering on the plastic sheet, for the manifest purpose of extending the useful life thereof. Where such reinforcing strips are conveniently available, it is desirable to mount the snap fasteners at the ends of such reinforcing strips.

The efficacy and operation of the device appears manifest from the description. The device is believed to be more efficient and convenient for the bed-ridden patient than known devices, since in removal and replacement of the holder and pads it is only necessary to release the snap fasteners 50, 59 and the body of the patient need only be slightly raised at the hips sufficiently to cleanse the parts, if necessary, and slip one end of a renewed holder or pad under the patient and then again connect the snap fasteners. The device is also simple, efficient and convenient for ambulatory persons, since the close fitting belt and dependent elastic suspenders draw the side flaps 26 and the holder 15 and pads closely into the critical area of the crotch, and the snap fasteners provide for a convenient changing of the pad without requiring removal of the wearing garments which are normally worn thereover; also, the well known form-fitting or form-retaining elastic girdle may be worn over the garment of the invention, which, because of the flat snug fitting of the belt and pad holder to the contour or anatomy, would not be apparent from the exterior of clothing; for the same reason the structure of the invention may also be worn either over or under a hernia truss. Because of the planar tapered or wedge shape of holder 15 and pads 16 they cover only the minimum essential skin area and thus permit ventilation, and also conserve use of material in formation of both holder and pads. It is also to be noted that when it is desired to change the entire garment for laundering, it is not necessary to manually handle the soiled part of the holder or the absorbent pads, since the end flaps 34, 35 of the holder may be opened and the holder manually held with the narrow end of the holder upwardly, whereupon, because of the wedge or tapered shape of the holder and pads, and especially the accentuated converging taper at the crotch, the pads will drop out of the wide end of the holder without manual contact.

Having described the invention, I claim:

1. In a sanitary garment of the character described, a holder member comprising a flexible moisture impervious elongated back sheet having moisture impervious side-edge flaps imperviously connected along the opposite longitudinal side edges of the back sheet, said side-edge flaps extending the entire length of the back sheet and inwardly over the face of the back sheet to freely overlie a substantial area of the back sheet adjacent the longitudinal edges of the back sheet and providing an elongated open area of the underlying back sheet between the opposed edges of said respective flaps, said holder being adapted to receive absorbent pads overlying the back sheet and underlying the side-edge flaps, a crotch portion between the ends of said holder, said crotch portion having an accentuated converging taper of the opposite side edges of the holder generally in the central area and between the ends thereof, and relatively spaced releasably cooperating fastener members secured to the face of the holder adjacent the opposite ends of its longitudinal side edges, a portion of said fasteners cooperating whereby flexible end portions may be retroverted upon itself and releasably secured to provide releasable moisture impervious pockets at opposite ends of pads within the holder, the corners of said pockets being so retroverted as to be moisture impervious.

2. A sanitary garment useful for incontinent persons as set forth in claim 1, and including a belt means for encircling the waist of a wearer and releasable connecting means between said belt and said holder, and in which the belt has depending dip portions at its lower edge adjacent the belt portions which normally overlie the hips, and elongated suspender means having one end connected to said belt and having releasable fastener members at the opposite end for releasably engaging cooperating fasteners adjacent to the respective opposite ends of the holder member.

3. In a sanitary garment useful for incontinent persons, the combination of a holder member comprising a flexible moisture-impervious elongated back sheet having retrovertible opposite end portions and [releasable fastener] means for securing said end portions in pocket-forming relation, side-edge flaps imperviously connected along the entire length of the longitudinal side edges of the back sheet, said side edge flaps extending inwardly to freely overlie a substantial area of the back sheet and providing an elongated open area of the underlying back sheet between the opposed edges of said respective flaps, said holder having a relatively wide portion at one of its ends and a relatively narrow portion at its opposite end, and a crotch portion between said end portions, the crotch portion having an accentuated converging taper of the opposite side edges of the holder generally in the central area between the said wider portion and said narrower portion, said narrower portion of the holder being of lesser width than the wider portion beyond said crotch, means for supporting said holder upon the person, and an absorbent pad having peripheral contour substantially similar to the peripheral contour of the holder when said holder had its opposite end portions retroverted to form end pockets having moisture impervious corners whereby said pad may snugly and releasably fit within said holder overlying the back sheet and underlying the side flaps and retroverted end portions.

4. A sanitary garment of the character described as set forth in claim 3 and in which the pad in said combination has a plurality of pad layers overlying in register, at least a portion of which have an opening adjacent the crotch portion providing a sump at a relatively narrow portion intermediate the ends of the pad.

5. A sanitary garment useful for incontinent persons as set forth in claim 4, and in which the pads having said sump opening are provided with a plurality of layers of absorbent material connected around the periphery of the sump by a seam which provides a crimped edge providing interstices between edges of overlying pad members around said sump.

6. In a sanitary garment of the character described an absorbent pad for mounting in a moisture-impervious holder member, said pad having a relatively wide portion at one of its ends and a relatively narrow portion at its opposite end and a crotch portion between said end portions, the crotch portion providing an accentuated converging taper of the opposite side edges of the pad between said wider portion and said narrow end portion, said pad having a plurality of pad layers overlying in register, at least a portion of which have an opening providing a sump adjacent the crotch portion, and wherein the pads having said sump are provided with a plurality of layers of absorbent material connected around the periphery of the sump by a seam which provides a crimped edge for forming interstices between edges of overlying pad members, the said seam being turned inwardly between the plurality of layers of absorbent material of such pad.

*7. A sanitary garment useful for incontinent persons as set forth in claim 3, wherein said means for securing said end portions in pocket forming relation comprise releasable fasteners.*

*8. In a sanitary garment useful for incontinent persons, the combination of a holder member comprising a flexible moisture-impervious elongated back sheet having retrovertible opposite end portions, means for securing said end portions in pocket-forming relation, side-edge flaps imperviously connected along the entire length of the longitudinal side edges of the back sheet, said side edge flaps extending inwardly to freely overlie a substantial area of the back sheet and providing an elongated open area of the underlying back sheet between the opposed edges of said respective flaps, said holder having a narrow crotch portion between its opposite end portions, and said longitudinal side edges having an accentuated converging taper of the opposite side edges of the holder from one of said end portions into said crotch portion, means for supporting said holder upon the person, and an absorbent pad having a peripheral contour similar to the peripheral contour of the holder when the holder has its opposite end portions retroverted to form end pockets, and fitted snugly and releasably within said holder over the back sheet and under the side flaps and retroverted end portions.*

* * * * *